United States Patent [19]

Pohl

[11] Patent Number: 4,631,120
[45] Date of Patent: Dec. 23, 1986

[54] METHOD IN WHICH ELEMENTAL PARTICLES ELECTROPHORETICALLY MIGRATE THROUGH A GEL ONTO A COLLECTING SURFACE OF A MOVING BELT

[76] Inventor: Fritz Pohl, Zähringer Platz 21, D-7750 Konstanz, Australia

[21] Appl. No.: 273,116

[22] Filed: Jun. 12, 1981

[30] Foreign Application Priority Data

Jun. 16, 1980 [DE] Fed. Rep. of Germany ....... 3022527

[51] Int. Cl.$^4$ ............................................ G01N 27/26
[52] U.S. Cl. ............................ 204/182.8; 204/180.1; 204/182.7; 204/299 R
[58] Field of Search ............ 204/182.8, 182.9, 299 R, 204/182.7, 300 R, 180.1

[56] References Cited

U.S. PATENT DOCUMENTS

| 3,497,441 | 2/1970 | Paksi | 204/182.8 |
| 3,533,933 | 10/1970 | Strauch | 204/182.8 |
| 3,764,513 | 10/1973 | Saravis | 204/182.8 X |
| 3,767,560 | 10/1973 | Elevitch | 204/182.8 X |
| 3,902,986 | 9/1975 | Nees | 204/182.8 X |
| 4,059,501 | 11/1977 | Strickler | 204/182.8 X |
| 4,111,785 | 9/1978 | Roskam | 204/182.8 X |

FOREIGN PATENT DOCUMENTS 3022527 12/1981 Fed. Rep. of Germany ... 204/180 G

Primary Examiner—John F. Niebling
Assistant Examiner—B. J. Boggs, Jr.
Attorney, Agent, or Firm—Roberts, Spiecens & Cohen

[57] ABSTRACT

A method in which an electrical field is applied through a gel to cause migration of elemental particles through the gel to an end region thereof and a belt having a collecting surface is advanced on the gel to collect the elemental particles and transport them with the belt.

24 Claims, 6 Drawing Figures

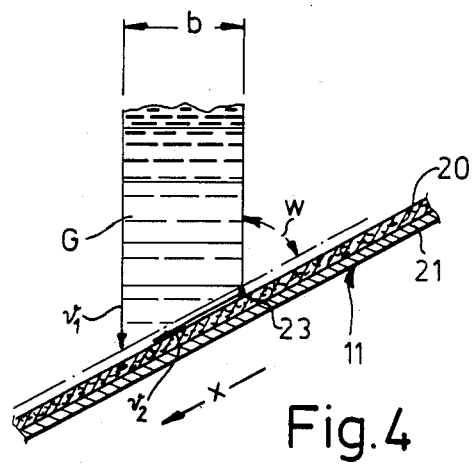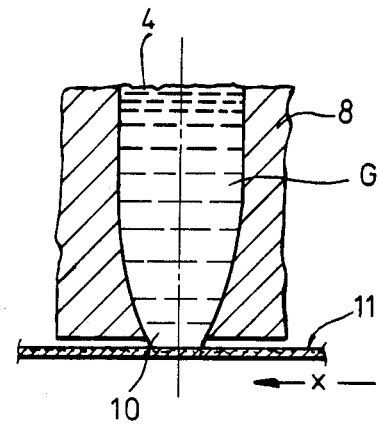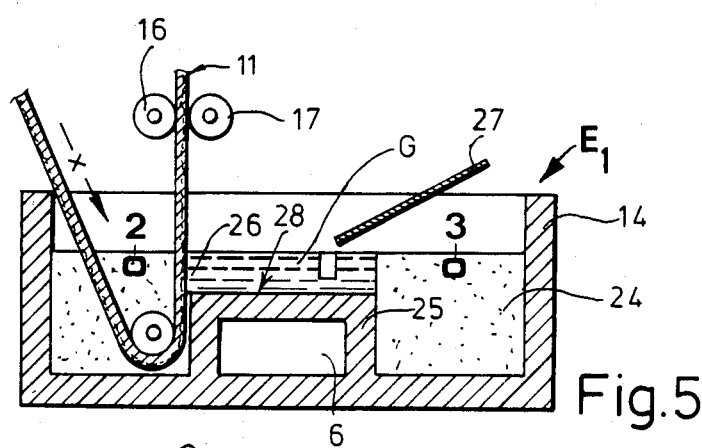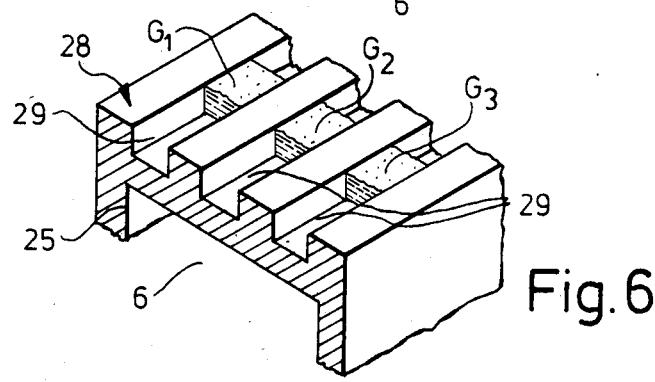

METHOD IN WHICH ELEMENTAL PARTICLES ELECTROPHORETICALLY MIGRATE THROUGH A GEL ONTO A COLLECTING SURFACE OF A MOVING BELT

The invention involves a method for performing electrophoresis in an electrical field, whereby molecules or particles are moved in a porous material, for example a gel, and which are, for example, made detectable by optical means.

BACKGROUND

Electrophoresis, an electrokinetic phenomenon, is used mainly in analytical and clinical chemistry for analyzing mixtures of substances, where one determines the different mobility of ions in an electric field. In addition, electrophoresis in porous media—such as polyacrylamide or agarose gels—has been developed as an important analytical and also preparative method in biochemistry and medicine, e.g., for separating complex mixtures of nucleic acids or proteins into single components.

After the application of an electrical field, different molecules move different distances into the gel (which includes all the substances suitable for this purpose) dependent on their mobility and are, thereby, separated in space. By specific staining of these molecules, their distribution in the mixture can be visualized and analyzed. A disadvantage is that the gel has to be removed from the electrophoresis apparatus and that it can be used only once. To achieve a satisfactory separation of many components—for example in the sequence analysis of DNA including up to a few hundred molecules of different lengths—gels of up to one meter length are currently used; further, a very high voltage has to be applied to obtain a large voltage gradient, which allows a separation within a reasonable time.

In preparative electrophoresis, a stationary collection chamber is usually provided at the end of the gel, into which the molecules move. This chamber is emptied from time to time and is then filled again; in this way, a stepwise separation of components of the mixture can be achieved.

The invention involves a method for performing electrophoresis in an electrical field, whereby molecules or particles are moved in a porous material, for example a gel, and which are, for example, made detectable by optical means. In addition, the invention involves an apparatus for accomplishing this process.

Electrophoresis, an electrokinetic phenomenon, is used mainly in analytical and clinical chemistry for analyzing mixtures of substances, where one determines the different mobility of ions in an electric field. In addition, electrophoresis in porous media—such as polyacrylamide or agarose gels—has been developed to an important analytical and also preparative method in biochemistry and medicine, e.g., for separating complex mixtures of nucleic acids or proteins into single components. After applying an electrical field, different molecules move different distances into the gel (which includes all the substances suitable for this purpose) dependent on their mobility and are, thereby, separated in space. By specific staining of these molecules, their distribution in the mixture can be visualized and analyzed. The disadvantage is that the gel has to be removed from the electrophoresis apparatus and that it can be used only once. To achieve a satisfactory separation of many components—for example in the sequence analysis of DNA up to a few hundred molecules of different lengths—gels of up to one meter length are used today; a very high voltage has to be applied to obtain a large voltage gradient, which allows a separation within reasonable time.

In preparative electrophoresis, a stationary collection chamber is usually provided at the end of the gel, into which the molecules move. This chamber is emptied from time to time and then filled again; in this way, a stepwise separation of components of the mixture can be achieved.

SUMMARY OF THE INVENTION

In view of the above, it is an object of the invention to provide an improved method for the electrophoresis so that the use of the apparatus simplified, the length of the gel reduced, and the whole procedure performed automatically, if required. To solve this problem in accordance with the invention is to provide at least one binding or collecting surface which moves continuously or which stepwise passes by in the area to which the molecules migrate, for example at the end of the porous substance (e.g., the gel). A further characteristic of the method of the invention is that the molecules are continuously collected on the binding surface due to ion exchange or reactive chemical groups.

The invention furthermore provides a device wherein at least one tape-like binding surface moves across the porous substance (e.g., the gel) and which is constructed as a continuously moving or circulating conveyer belt (hereafter termed as "the tape").

This conveyer belt may consist of several layers; the layer facing the gel is used for binding the molecules, while another layer supports the binding surface. This allows, for example, the use of binding surfaces of minor mechanical strength which are supported by a plastic net moved by a driving unit.

Especially useful are binding surfaces consisting of paper, foils or similar material, which have a surface charge opposite to that of the ionic molecules, or binding surfaces with reactive chemical groups for covalent or non-covalent binding of molecules.

In a rather short and solid porous phase, which is denoted herein as gel (such as polyacrylamide gel, agarose gel, paper, foil, or similar substances) to which a direct current is applied, the charged molecules or particles move according to their mobility to the end of the gel and are bound there to the moving tape, that is at the charged surface (ion-exchange paper) or the reactive chemical groups thereof. According to another characteristic of the invention, the tape can be moved through a fixation or staining bath so that the components become visible and can be recorded. It is also within the purpose of the invention to elute and collect single components and to use conditions where any interaction between particles and tape is eliminated.

The width of an eluted component on the tape or conveyer-belt will be smaller the thinner the gel, so that, for analytical problems, gels as thin as possible should be used. However, according to a further characteristic of the invention, components can be concentrated by forming an angle between the direction of the eluting and moving particles and the direction of the moving tape. The binding surface collects the molecules first at the point where it touches the gel and, while it moves on, the particles are eluted and bound at the same point. This may be important for analytical purposes, but in particular is important for preparative purposes. On the other hand, it is possible to distribute a component over a large area by using a high tape velocity, thereby overcoming possible limitations in the binding capacity.

The use of a movable tape onto which particles or molecules are bound after leaving the gel adds an additional dimension to electrophoretic separations. The distance between components on the tape can be easily varied by changing the tape velocity. Furthermore, the relative position of components on the tape can be varied by programming the tape velocity, the voltage gradient, or the temperature.

Use of different materials for the tape, which may contain more than one layer, is within the scope of the invention. Thus, detection methods such as staining, radioactivity, etc., are no longer bound to the gel material, which results in higher flexibility.

An especially important feature of the invention is that a separation is achieved between electrophoresis and detection on the tape, allowing one to activate reactive groups immediately before use, while not only staining or other analytical procedures, but also elution of bound molecules or particles after electrophoresis can be done in a continuous, automatic process in different baths or devices. The tape can be washed after analysis or elution and used again, which allows material to be saved.

After all components of a mixture have left the gel, a new mixture can be applied to it. Thus, considerable savings in material and preparation time for gels are possible and the separations become more reproducible. Use of short gels, as mentioned before, also saves material and offers the additional advantage that the time during which fast-moving molecules remain in the gel is shortened, the diffusion minimized, and the separation improved. The total voltage for achieving a certain voltage gradient can be reduced for short gels, thus improving security, decreasing energy demand, and allowing for simple removal of the generated heat.

The molecules of a component can be geometrically concentrated in the contact area between gel and tape to a zone narrower than the thickness of the gel. This can result in higher analytical sensitivity and better resolution for preparative separations.

Of advantage is to position the gel in a vertical shaft with an opening facing the conveyer belt. The length of the opening can be chosen so that a number of parallel conveyer belts are possible, which may move at different speeds. It may also be of advantage to employ a triangular opening, so as to make it narrower on one side of the tape or above the adjacent tapes; such a configuration offers new possibilities when a number of parallel tapes are employed. Furthermore, for the use of different gels in parallel, a gel-bearing surface with a number of parallel grooves has proved to be favorable.

In practice, it has been shown that the method and device according to the invention can be used for analytical, as well as for preparative separations, and thus considerably expand the field of applications.

BRIEF DESCRIPTION OF DRAWING

Further advantages, characteristics and details of the invention appear in the following description of preferred embodiments and in the drawing in which:

FIG. 3 is an enlarged cross-section of a detail of a device according to the invention;

FIG. 4 is another detail of a device of the invention;

FIG. 5 is a different design of the device of the invention;

FIG. 6 is a diagonal view of a detail of another design.

DETAILED DESCRIPTION

Figure 1:
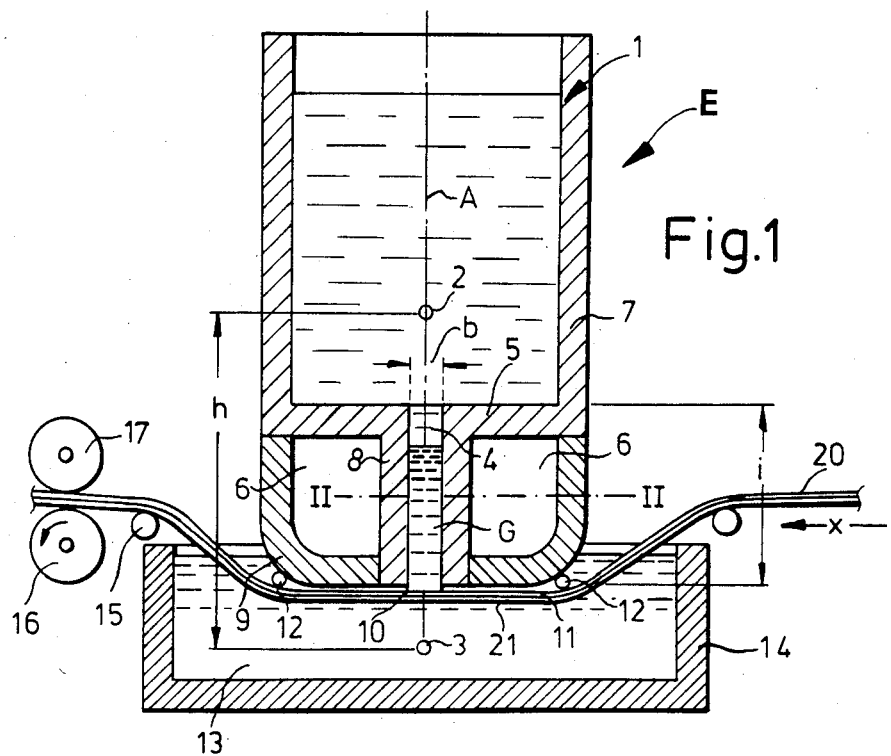
FIG. 1 is a schematic cross-section of a device according to invention.

In FIG. 1, a buffer vessel 1 of an apparatus E for performing electrophoresis in accordance with the invention incorporates at its axis A an electrode 2 which, together with a second electrode 3 at a distance h below, creates an electrical field (not shown). Within its range is a vertical shaft 4 of width b and height i for the gel G.

At both sides of the shaft, which ends at the bottom of the vessel 5, chambers 6 are provided for temperature control. In FIG. 1, the walls 7 of the vessel 1 are parallel to the walls 8 of the shaft 4 and are connected at their lower ends by the curved outer walls 9 of the chambers. A tape 11 is positioned below the opening 10 of the shaft 4, which moves over the roller 12 in a horizontal direction as shown by the arrow x below the opening 10 of the shaft 4. The tape 11 and the opening 10 are summerged in the solution 13 contained in the vessel 14.

The tape 11 leaves the solution 13 across the guide pulley 15 and its movement is controlled by a driving shaft 16 and a pressure roller 17. The ions leaving the gel G are bound on a filter layer 20 (e.g., filter paper) of the tape 11 and leave the solution 13 horizontally. The filter layer 20 is carried by a supporting net 21.

Figure 2:
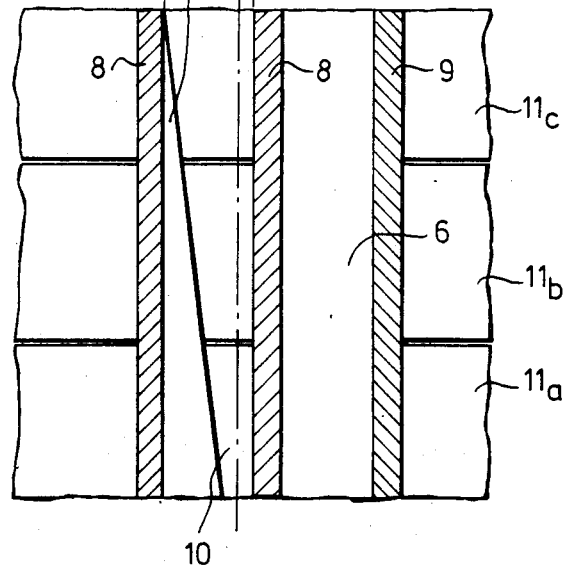
FIG. 2 is a top view a top-view of an enlarged detail of another device of the invention, along line II—II in FIG. 1.

While the width b of the shaft 4 is constant in the device E of FIG. 1, FIG. 2 shows an opening 10 of the shaft 4, the width $b_1$ of which increases toward one of the vessels, with several tapes 11a, 11b, and 11c moving below the opening.

The single-layer tape 11 in FIG. 3 is below a shaft 4, the width of which narrows toward the opening 10.

FIG. 4 shows a two-layer tape 11 at an angle w with respect to the gel G, first touching the gel at 23. The ions of the gel area at distance b from 23 arrive at tape 11 later, at a position that depends on their velocity $v_1$ and the tape velocity $v_2$.

In another example of a device according to the invention, the tape 11 moves vertically (FIG. 5); it runs through a fixing or washing bath 24 and touches the gel G, which rests on the tunnel 25, at a vertical area 26. The mixture in this device $E_1$ is applied via 27.

FIG. 6 shows a top surface 28 of tunnel 25 with a number of grooves 29 for using different gels $G_1$, $G_2$, $G_3$.

I claim:

1. A method of performing electrophoresis comprising electrophoretically producing migration of elemental particles through a porous substance to a collection region thereof, transporting a belt having a collecting surface past said collection region of said porous substance and collecting said elemental particles from said collection region onto said collecting surface for transport with said belt away from the porous substance.

2. A method according to claim 1 wherein said belt is moved continuously.

3. A method according to claim 1 wherein said particles are collected on said collecting surface by being bound to the collecting surface by ion-exchange.

4. A method according to claim 1 wherein said particles are collected on said collecting surface by being bound to reactive chemical groups on the collecting surface.

5. A method according to claim 1 comprising moving the belt through a bath after contacting the porous substance.

6. A method according to claim 5 wherein the elemental particles are stained in said bath.

7. A method according to claim 5 wherein the elemental particles are fixed to the collecting surface in said bath.

8. A method according to claim 1 wherein said belt is transported perpendicularly to said collection region.

9. A method according to claim 1 wherein said belt is transported at an angle relative to the direction of migration of said elemental particles through said porous substance.

10. A method according to claim 1 wherein the belt is transported at a velocity which is program-controlled.

11. A method according to claim 1 comprising passing the belt through a cleaning bath after contacting the porous substance.

12. A method according to claim 1 wherein the porous substance is a body of gel having an end to which said elemental particles migrate, said collecting surface of said belt contacting said end of the body of gel.

13. A method of performing electrophoresis comprising electrophoretically producing migration of elemental particles through a porous substance to a collection region thereof, collecting elemental particles from said collection region on a collection surface adjacent said collection region, and transporting said collection surface away from said porous substance at a determined velocity on a moving belt.

14. A method according to claim 13 wherein said particles are collected on said collecting surface by being bound to the collecting surface by ion-exchange.

15. A method according to claim 13 wherein said particles are collected on said collecting surface by being bound to reactive chemical groups on the collecting surface.

16. A method according to claim 13 comprising moving the belt through a bath after contacting the porous substance.

17. A method according to claim 16 wherein the elemental particles are stained in said bath.

18. A method according to claim 16 wherein the elemental particles are fixed to the collecting surface in said bath.

19. A method according to claim 13 wherein said belt is transported perpendicularly to said collection region.

20. A method according to claim 13 wherein said belt is transported at an anle relative to the direction of migration of said elemental particles through said porous substance.

21. A method according to claim 13 wherein the velocity of said belt is program-controlled.

22. A method according to claim 13 comprising passing the belt through a cleaning bath after contacting the porous substance.

23. A method according to claim 13 wherein the porous substance is a body of gel having an end to which said elemental particles migrate, said collecting surface contacting said end of the body of gel.

24. A method according to claim 13 wherein said collection surface is a flat solid material onto which said elemental particles become fixed, said collection surface being secured with said belt.

* * * * *